United States Patent
Chen et al.

(10) Patent No.: US 6,683,313 B2
(45) Date of Patent: Jan. 27, 2004

(54) ULTRAVIOLET WATER STERILIZATION DEVICE IN A MODULARIZED CONFIGURATION

(75) Inventors: Jian Chen, Fujian (CN); Ziji Yan, Fujian (CN)

(73) Assignee: Fujian Newland Entech Co., Ltd., Fuzhou (CN)

( * ) Notice: Subject to any disclaimer, the term of this patent is extended or adjusted under 35 U.S.C. 154(b) by 65 days.

(21) Appl. No.: 09/951,323

(22) Filed: Sep. 13, 2001

(65) Prior Publication Data

US 2002/0043504 A1 Apr. 18, 2002

(30) Foreign Application Priority Data

Sep. 14, 2000 (CN) .......................... 00221777 U
Jan. 22, 2001 (CN) .......................... 01210375 U
Feb. 24, 2001 (CN) .......................... 01105461 A
Feb. 24, 2001 (CN) .......................... 01105462 A

(51) Int. Cl.$^7$ .................. G01N 23/00; G01N 29/01; B01D 17/06; A61L 2/00; B01J 19/08

(52) U.S. Cl. .................. 250/455.11; 250/435; 250/436; 210/748; 422/24; 422/186.3

(58) Field of Search .................. 250/455.11, 435, 250/436, 428, 437; 422/24, 186.3; 210/256, 748

(56) References Cited

U.S. PATENT DOCUMENTS

| | | | | |
|---|---|---|---|---|
| 5,290,439 A | * | 3/1994 | Buchwald | 210/198.1 |
| 5,302,356 A | * | 4/1994 | Shadman et al. | 422/186.3 |
| 5,352,359 A | * | 10/1994 | Nagai et al. | 210/192 |
| 5,888,388 A | * | 3/1999 | Kirk | 210/170 |

FOREIGN PATENT DOCUMENTS

CN   96 2280968   6/1997   ............. C02F/1/32

* cited by examiner

*Primary Examiner*—Benjamin R. Fuller
*Assistant Examiner*—Alfred E. Dudding
(74) *Attorney, Agent, or Firm*—Ladas & Parry

(57) ABSTRACT

This Invention relates to a ultraviolet water sterilization device having a sterilization chamber module into a modularized configuration each module having two water-through ports, one port is used as a water inlet and the other port as an outlet of the sterilization chamber. The sterilization chamber may be formed into a single-wall configuration or a casing configuration. Inside the sterilization chamber are distributed n≧1 ultraviolet lamps with glass sleeves. Each chamber module may be used individually or in combination of two, three or more modules in a large chamber to meet the need of sterilization for a large water volume. Each module can be also arranged in separate sections so as to lessen manufacturing difficulties and simplify the assembly process.

10 Claims, 5 Drawing Sheets

ULTRAVIOLET WATER STERILIZATION DEVICE IN A MODULARIZED CONFIGURATION

BACKGROUND OF THE INVENTION

This invention relates to a water sterilization device and in particular to an ultraviolet (UV) water sterilization device in a modularized configuration.

DISCUSSION OF THE PRIOR ART

Presently, there are two types of ultraviolet sterilization devices, one type is an open-channel sterilization reactor, and the other type is closed. The open-channel sterilization reactor is often employed for sterilization of a large flow of waste water. The closed sterilization reactor, especially using a low-pressure mercury lamp, is mainly employed for sterilization of a small amount of water used in varied areas, but is not applicable for the sterilization of water treated in a large volume with high quality. In general, the treatment capacity of a single device is relatively small, and undoubtedly and at least partly it will waste resources if a plurality of devices is combined into use. For this reason, an ultraviolet water sterilization device capable of treating a large volume is needed.

Patent application No. ZL 96228096.8 discloses a water-through ultraviolet sterilization device, including a water-through chamber comprising of three sleeves of quartz glass disposed concentrically and permitting reciprocal flow of water flow. This device has the advantages of low energy loss and high efficiency, but is structurally complicated and inconvenient for handling and maintenance. The sleeves of quartz glass cannot sustain vibration during transportation and operations especially, if the ultraviolet sterilization device needs to be disassembled in order to remove scale after operation for a period of time. This complicated structure induces inconvenience, for cleaning and maintenance. If it is necessary to increase the water volume through the sleeves of quartz glass having a single light source, the diameter of the sleeves will need to be increased, and so will the sleeve wall thickness, thus the absorption by the sleeves of ultraviolet rays will be increased, decreasing the penetrating distance in water of the ultraviolet rays and consequently decreasing the ultraviolet radiation dose accepted by water flowing through the outer and intermediate sleeve. The decreased UV dose decreases the kill effect on bacterium and viruses. Therefore, this device is not applicable for the sterilization treatment of a large volume of water.

SUMMARY OF THE INVENTION

The object of this invention is to provide a UV water sterilization device for a large volume of water. By use of an ultraviolet water sterilization system composed of the said sterilization devices in a modularized configuration, the deficiencies of the device that the treatment volume is small, and handling and maintenance are inconvenient, can be eliminated. Water sterilization with high efficiency and large volume can thus be achieved.

The object of this invention is achieved by forming the sterilization chamber into a modularized configuration each having two water-through ports. When this module is employed individually, one port is used as a water inlet and the other as an outlet of the sterilization chamber. The sterilization chamber may be formed as a single-wall configuration or a sleeve-casing configuration. Inside the sterilization reacting chamber are distributed $n \geq 1$ one or more ultraviolet lamps with glass sleeves that are used to protect the ultraviolet lamps. One end of the ultraviolet lamp and the glass sleeve is located on a main positioning plate for the ultraviolet lamp. The scaling fitting and nut of the glass sleeve seal the juncture between the glass sleeve and the main positioning plate The main positioning plate of the ultraviolet lamp is secured on the end surface of the sterilization chamber by bolts and nuts. Each chamber module may be used individually or in combination of with two, three or more modules in a large chamber to meet the length of the UV lamps and the need for sterilization of a large volume of water. The connection between two modules, or between a module and inlet pipe or outlet pipe, is formed by a feasible joint or a flange with a sealing gasket and allows the water inlet and water outlet to be arranged at any rotational angle around a longitudinal axis with respect to each other. Each module can be also arranged as separate sections to lessen the manufacturing difficulties and simplify the assembly process. The sterilization chamber may be made as a cylinder or any other shapes.

This invention may be brought about by two plans; plan 1 is a sterilization chamber in a sleeve-casing configuration, and plan 2 is a sterilization chamber in a single-wall configuration.

The sterilization chamber in a sleeve-casing configuration for plan 1 has a water inlet or water outlet, or both, formed into a casing configuration, namely, a double-wall configuration. The inner chamber wall of the casing configuration is provided on the end portion with an auxiliary water passage that communicates with an outer casing. The water through port of the outer casing is directly connected to the inlet pipe or outlet pipe, and the auxiliary water-through passage positioned at the end portion of the inner chamber wall is located inside the outer casing. The auxiliary water-through passage is designed in two ways: one way is that the end surface of the inner chamber wall is sealed, while the side surface is provided with several auxiliary water-through orifices, which have a cross-sectional area which are equal to or similar to the area of the water passage port of the outer casing communicating therewith; the other way is that the end surface of inner chamber wall is not sealed and is directly used as an auxiliary water-through passage, which cross-sectional area is equal to or similar, to that of the inner chamber or the water-through port of the outer casing communicating therewith. The sterilization chamber in the casing configuration can also be arranged in separate sections, one section being a water-through part in a casing configuration, the other is section being a pipe spool, both being connected to form an integrated module A with number of water-through parts and pipe spools which are combined when a sterilization chamber is formed. The sterilization chamber in the casing configuration is arranged as a module that can be used individually or in combination with two, three or more modules. The connection between modules can be formed by a feasible joint or a flange with a sealing gasket which allows the water inlet to be arranged at any rotational angle relative to the water outlet.

The sterilization reacting chamber in the single-wall configuration for plan 2 has the sterilization chamber formed into a chamber with a single wall, which has two water-through ports; one port is used as a water inlet, the other port as a water outlet. The ultraviolet lamps are distributed inside the sterilization chamber. The sterilization chamber in the single-wall configuration can be also arranged in separate sections, namely, one water-through port and one pipe spool matched thereto. A number of water-through parts and pipe spools can be combined when the sterilization chamber is formed. The sterilization chamber is arranged as a module. The module can be sized in different water-through lengths and diameters, and can be used individually or in combination with two, three or more modules. The connection between modules allows the water inlet to be arranged at any rotational angle relative to the water outlet.

Here two embodiments are respectively provided for plan 1 and plan 2. The first embodiment of plan 1 is a sterilization chamber in which the water inlet or water outlet is formed into a casing configuration, and the second embodiment is a sterilization chamber which both the water inlet and water outlet are formed into casing configurations The first embodiment of plan 2 is a sterilization chamber in a single integral module, and the second embodiment is a sterilization chamber formed with several separate modules.

The specific embodiments according to this invention will be further described in conjunction with the accompanying drawings.

BRIEF DESCRIPTION OF THE DRAWING FIGURES

Figure 3A:
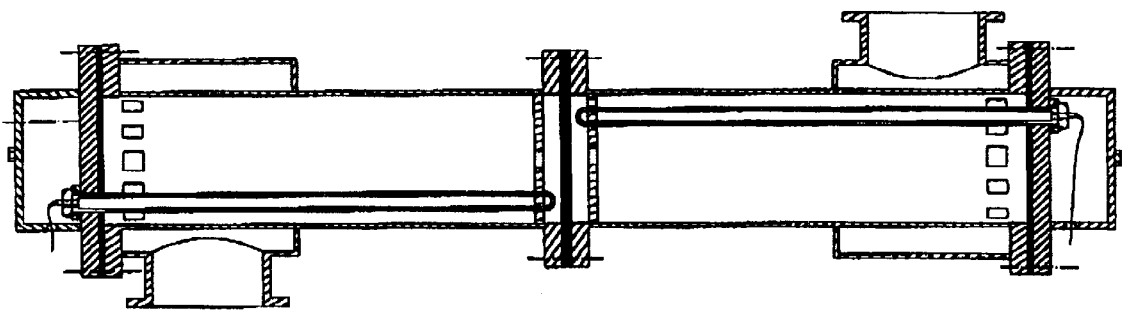
Figure 3B:
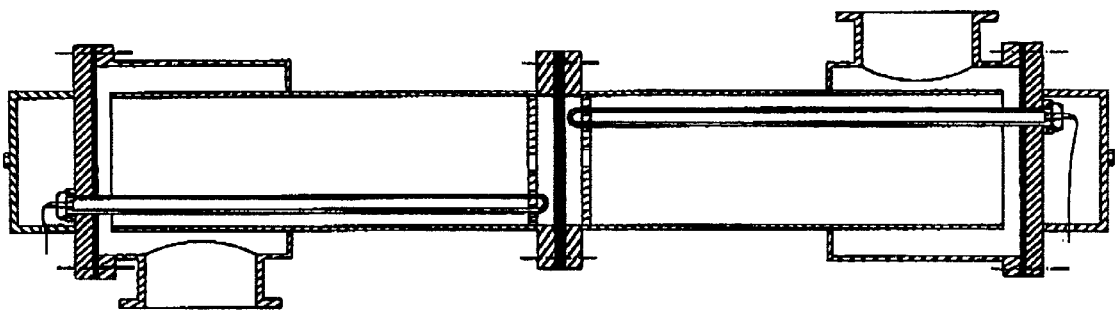
Figure 4A:
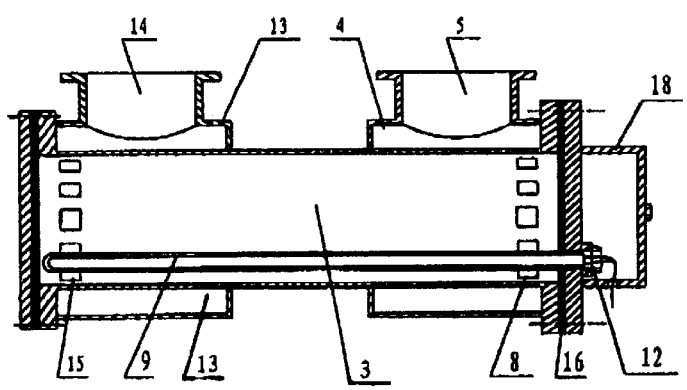
Figure 4B:
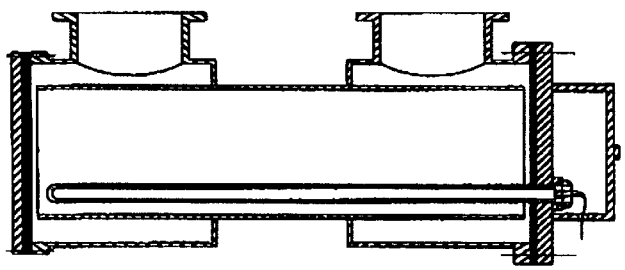
Figure 6A:
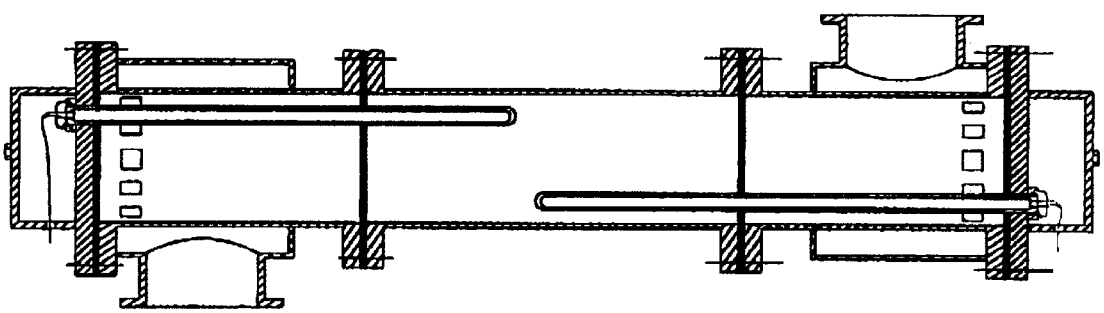
Figure 6B:
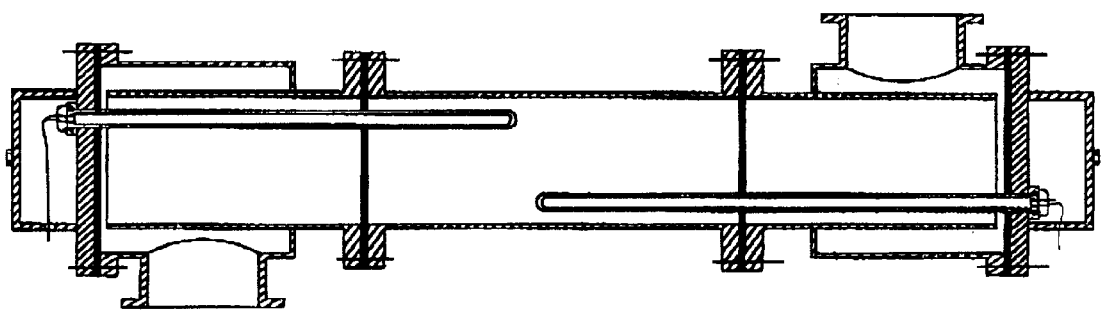
Figure 7:
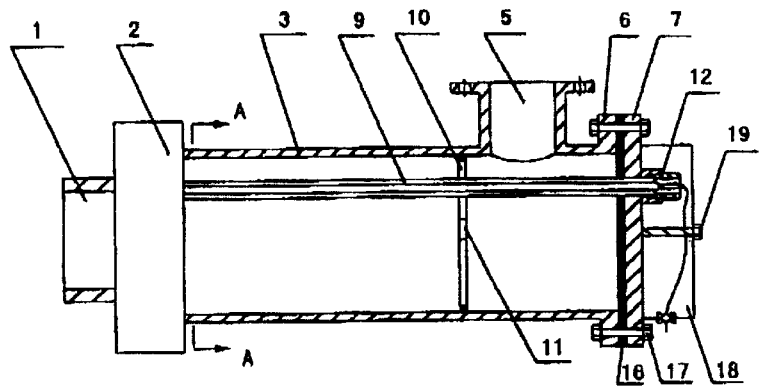
Figure 8A:
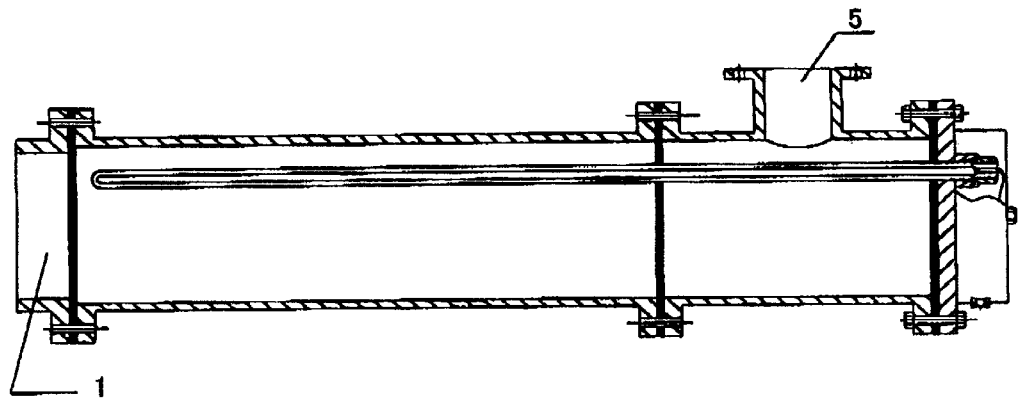
Figure 8B:
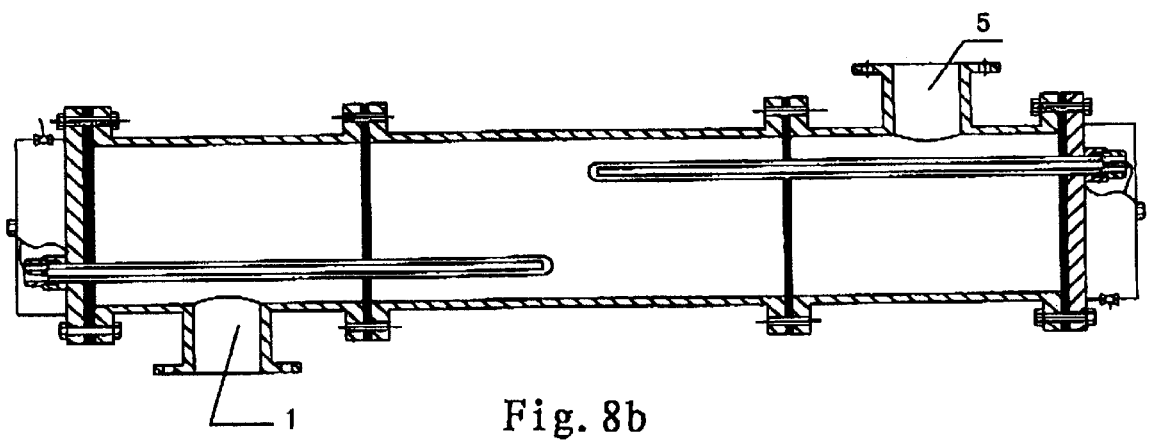

FIGS. 3a and 3b are a schematic view of Me first embodiment for plan 1 according to this invention showing the connection of a sterilization chamber, FIGS. 4a and 4b are a main section view of the second embodiment for plan 1 according to this invention showing a sterilization chamber;

FIGS. 5a1, 5a2, 5b1 and 5b2 are a schematic view of the first embodiment for plan 1 according to this invention showing a sterilization chamber formed in separate sections;

FIGS. 6a and 6b are a schematic view of the second embodiment for plan 1 according to this invention showing the sterilization chamber formed in separate sections;

FIG. 7 is a section view of the first embodiment for plan 2 according to this invention showing an integral module;

FIGS. 8a and 8b are a schematic view of the second embodiment for plan 2 according to this invention showing the connection between separate modules.

In the drawings, reference number 1 denotes a water inlet; 2 denotes a flange seat B at the end of the sterilization chamber, 3 denotes a sterilization chamber; 4 denotes an outer casing of the water outlet; 5 denotes a water outlet; 6 denotes flange seat A at the other end of the sterilization chamber; 7 denotes a main positioning plate; 8 denotes an auxiliary water-through orifice; 9 denotes an ultraviolet lamp with a glass sleeve; 10 denotes a positioning plate of the glass sleeve; 11 denotes a water-through hole in the positioning plate of the glass sleeve; 12 denotes a sealing fitting of the glass sleeve; 13 denotes an outer casing of the water inlet; 14 denotes a water inlet; 15 denotes an auxiliary water-through orifice; 16 denotes a sealing gasket; 17 denotes a bolt and nut; 18 denotes a protective cover of the power supply; and 19 denotes a bolt and nut for the protective cover of the power supply.

Figure 1A:
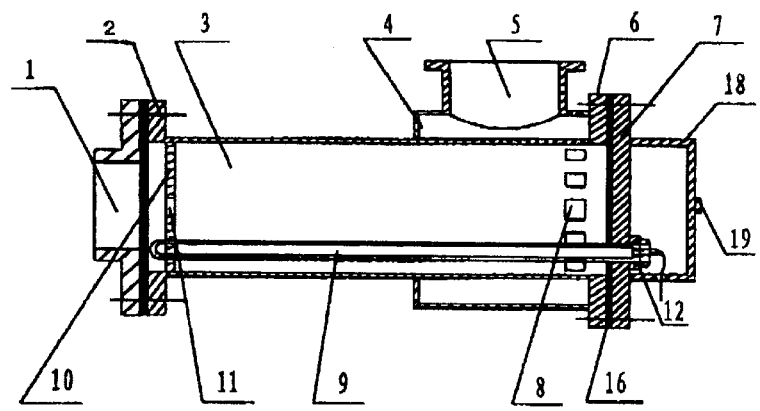
FIGS. 1a and 1b are a main section view of the first embodiment for plan 1 according to this invention showing a sterilization chamber.
Figure 1B:
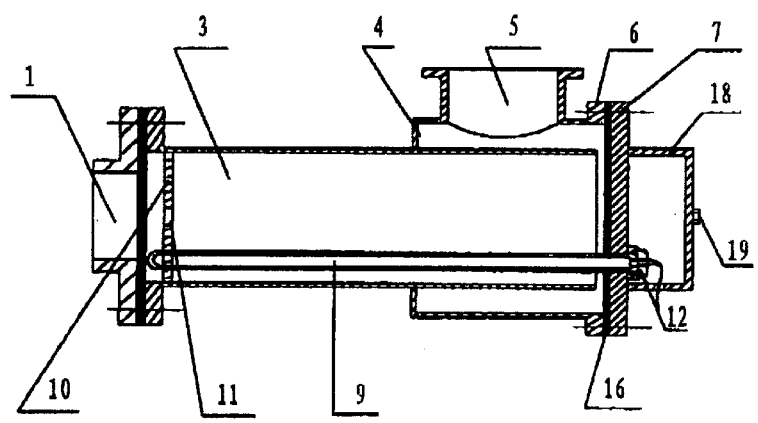
Figure 2:
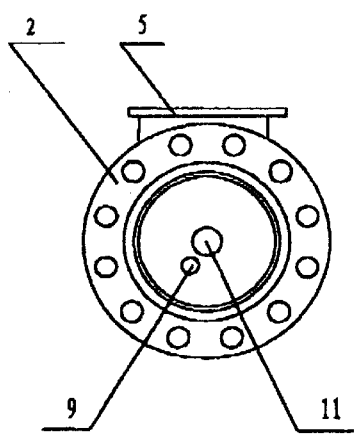
FIG. 2 is a left view of the first embodiment for plan 1 according to this invention showing a sterilization chamber.
Figure 5A:
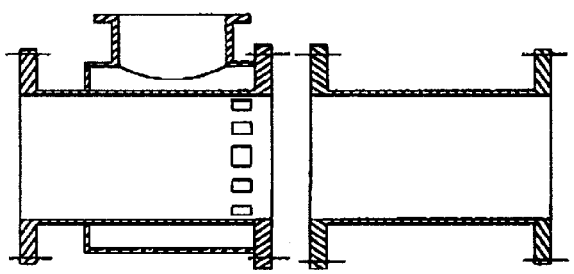
Figure 5A:
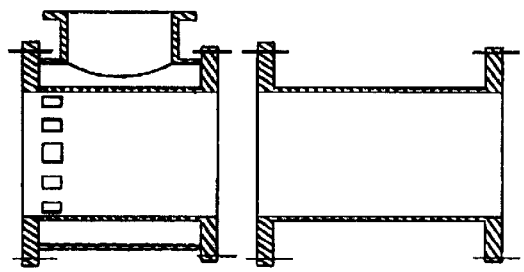
Figure 5B:
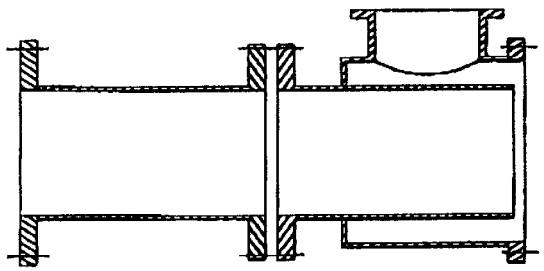
Figure 5B:
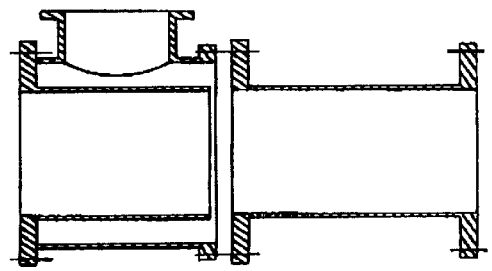

The first embodiment of plan 1 according to this invention is described as follows. In this embodiment, as shown in FIGS. 1a, 1b and 2, the sterilization chamber is made in a cylindrical shape and has a water outlet is formed in a sleeve-casing configuration. The sterilization device consists of a water inlet 1, a sterilization chamber 3 and a water outlet 5. The n≧1 one or more UV lamps with glass sleeves 9 used to protect the UV lamps are distributed inside the sterilization chamber. The sealing fitting 12 of glass sleeve seals the juncture between a glass sleeve 9 of the UV lamp and the main positioning plate 7. A casing configuration is formed into the water outlet in order to meet the need for large water volume. For the sterilization chamber in FIG. 1a, the end surface of inner chamber wall is sealed and on the cylindrical wall several auxiliary water-through orifices 8 are provided inside the outer casing 4 of the water outlet, the total cross-sectional area of the water-through orifices is equal to or similar to the cross-sectional area of the water inlet 1 or the water outlet 5. In FIG. 1b, the end surface of inner chamber wall of a the sleeve casing configuration is not sealed and is directly used as an auxiliary water passage. The cross-sectional area of the water inlet 1 is equal to or similar to the cross-sectional area of the inner chamber and the cross-sectional area of the outer casing of the water outlet inside which the auxiliary water-through passage is located. If a long UV lamp is mounted with glass sleeve 9, it is necessary to use a positioning plate 10 on the glass sleeve to support the UV lamp within glass sleeve 9. One end surface of the outer casing of the water outlet is sealed to the wall of the sterilization chamber; the other end is secured by a connecting flange. In this embodiment, the water outlet can be used as a water inlet instead, namely, the water inlet is formed as a casing configuration. This module can be used individually or in combination with two, three or more modules. The schematic view of the connection of modules is shown in FIGS. 3a and 3b. The module can also be designed in separate sections as shown in FIGS. 5a and 5b. FIG. 5a shows a main water-through port in a casing configuration with a pipe spool matched thereto, in which the water-through orifices are arranged in the inner wall of the casing configuration. FIG. 5b shows a main water-through port in a casing configuration with a pipe spool matched thereto, in which the end surface of the inner chamber wall is not sealed. Both above configurations are adapted to pipe spools by a connecting flange. A varying number of the main water-through port and pipe spools can be combined into use. The main water-through port in the casing configuration can be constructed as a partial casing configuration as shown in FIG. 5a1, or as a fill casing configuration as shown in FIG. 5a2. In addition, the connecting flange seat 2 can be provided with several connecting holes being evenly spaced around its circumference so that when a plurality of modules is combined into use or arranged in separate sections, the water inlet may be arranged relative to the water outlet at any rotational angle if the modules are connected.

Second Embodiment of Plan 1

In this embodiment as shown in FIGS. 4a and 4b, the sterilization chamber is made in a cylindrical shape and both its water outlet and water inlet are formed into a casing configuration. The sterilization device consists of a outer casing 13 on water inlet 14, a sterilization chamber 3 and an outer casing 4 on water outlet 5. As shown in the figure, both water inlet and water outlet are formed into the casing configuration in order to meet the need for large water volume. The n≧1 UV lamps with glass sleeves 9 used to protect the UV lamps are distributed inside the sterilization chamber. The sealing fitting 12 on the glass sleeve seals the juncture between the glass sleeve 9 of the UV lamp and the main positioning plate 7. As shown in FIG. 4a, the end portions of the said inner wall the sterilization chamber in the casing configuration is provided with several auxiliary water-through orifices 8 and 15, and the water-through cross-sectional area of orifices 8 or 15 are totally equal to or similar to the cross-sectional area of water inlet 1 or water outlet 5. In this figure, one end surface of the outer casing 4 of the water outlet is sealed to the wall of the sterilization chamber 3, and the other end surface is secured to a connecting flange. All auxiliary water-through orifices 8 are located inside outer casing 4 of the water outlet, and all of auxiliary water-through orifice 15 am is located inside outer casing 13 of the water inlet. The sealing connection is formed by welding or in another way. As shown in FIG. 4*b*, the end surface of the inner wall is not sealed and is directly used as an auxiliary water passage. The water-through cross-sectional area of the end surface is equal to or similar to the inner cross-sectional area of the cylindrical chamber. One end surface of the outer casing is sealed to the wall of the sterilization chamber and the other end surface is secured by a connecting flange.

The sterilization chamber in the casing configuration may be also arranged in separate sections, namely, a water-through part in the casing configuration and a pipe spool matched thereto, as shown in FIGS. 5*a* and 5*b*. A different number of water-through parts and pipe spools can be combined into use when the sterilization chamber is constructed. FIGS. 6*a* and 6*b* are a connection view showing the combined sterilization chamber of having separate sections.

The ultraviolet sterilization device in the first embodiment of plan 2 according to this invention is shown in FIG. 7. In this embodiment, the sterilization chamber is formed into a single-wall configuration which may be made in a cylindrical shape or not. Within the sterilization chamber are distributed n≧1 UV lamps with glass sleeves 9 mounted on a main positioning plate 7 of the UV lamp at one end. A positioning plate 10 of the glass sleeve is arranged inside the sterilization chamber to support the glass sleeves If a long lamp is used. The main positioning plate 7 of the UV lamp is secured on the flange seat at the end of the sterilization chamber by tightening bolts and nuts 17 of the plate. A protective cover 18 on the power supply is secured on the outer side of main positioning plate 7 of the UV lamp by the tightening bolts 19 for the protective cover The water inlet, water outlet and the end portion of the sterilization clamber can be connected by a feasible joint or a flange with a sealing gasket. The water-through length and diameter of the module may be made in different sizes to create a series of modules. The module can be used individually or in combination with two, three or more modules. Several connecting holes evenly spaced around the circumference of the connecting flanges are provided so that the water inlet can be arranged relative to the water outlet at any radial angle when the flanges are connected. The connection between modules, between a water-through and inlet pipe or outlet pipe can be formed by a feasible joint or connecting flange 2.

Second Embodiment of Plan 2

The ultraviolet water sterilization device in the second embodiment of plan 2 is shown in FIGS. 8*a* and 8*b*, in which the sterilization chamber is formed into a single-wall configuration in separate sections. FIG. 8*a* is a schematic view showing the connection between a main water-through port section of a module and a pipe spool matched thereto; FIG. 8*b* is a schematic view showing a connection between a main water-passing port of a module containing a water inlet 1 and water outlet 5, and a pipe spool matched thereto. The main water-through part is combined with the pipe spool to form an integrated module. The advantage in forming separate sections lies in that the main water-through part can be made of other materials, such as a ceramic material, other than a stainless steel so as to reduce cost, lessen manufacturing difficulties and simplify the assembly process. A different number of main water-through parts and pipe spools matched thereto can be selected to construct a sterilization chamber. FIGS. 8*a* and 8*b* are a schematic view showing a connection of a sterilization chamber in a single-wall configuration in separate sections.

The ultraviolet sterilization device in a modularized configuration according to this invention may be used for the sterilization of seawater, drinking water and treated foul water as well as other appropriate liquids, and also may be used for the sterilization of a gas. The term fluid as used within this application encompasses both liquids and gases. The water treatment volume of the ultraviolet sterilization device will be greatly increased because of the modularization arrangement, and its handling and maintenance will be more convenient.

The embodiments according to this invention have been described with reference to the accompanying drawings and can be made in various modifications by those skilled in the art without departing the scope of the appended claims.

What is claimed is:

1. An ultraviolet fluid sterilization device comprising:
   a sterilization chamber having a first end opening and a second end opening provided on opposite ends of said chamber;
   an inlet/outlet orifice in communication with said sterilization chamber;
   one or more UV lamps mounted within said sterilization chamber; and
   a connection means provided at each of said first end opening and said second end opening;
   wherein said connection means couples an end opening of said sterilization device to another end opening of another sterilization device or additional module;
   wherein said connection means receives an end cap;
   wherein at least one end of the sterilization chamber is formed in a casing configuration; and
   wherein said inlet/outlet orifice is provided and formed in said casing configuration, and auxiliary water-through ports are provided through said sterilization chamber at said inlet/outlet orifice casing.

2. The ultraviolet fluid sterilization device of claim 1 wherein two inlet/outlet orifices are provided through a wall of said sterilization chamber.

3. The ultraviolet fluid sterilization device of claim 1 wherein said connection means is a flange.

4. The ultraviolet fluid sterilization device of claim 1 wherein said connection means is a feasible joint.

5. The ultraviolet fluid sterilization device of claim 1 wherein said UV lamps are mounted in place within said sterilization chamber by a glass sleeve.

6. The ultraviolet fluid sterilization device of claim 5 wherein a positioning plate secures said UV lamps to said glass sleeve, and a sealing fitting is provided between said glass sleeve and said UV lamps.

7. The ultraviolet fluid sterilization device of claim 1 wherein two inlet/outlet orifices are provided and formed in said casing configuration.

8. The ultraviolet fluid sterilization device of claim 1 wherein the cross-sectional areas of each of the end openings and inlet/outlet orifices is equal to the cross-sectional area of the auxiliary water-through ports at each casing.

9. The ultraviolet fluid sterilization device of claim 1 wherein said sterilization chamber is cylindrical in shape.

10. The ultraviolet fluid sterilization device of claim 1 wherein said connection means allows the inlet/outlet orifice to be rotationally disposed at any angle about a longitudinal axis relative to the inlet/outlet orifice of another axially coupled sterilization device.

* * * * *